United States Patent
Kent et al.

(10) Patent No.: US 10,668,017 B2
(45) Date of Patent: Jun. 2, 2020

(54) PERIVASCULAR DRUG DELIVERY SYSTEM

(71) Applicant: Wisconsin Alumni Research Foundation, Madison, WI (US)

(72) Inventors: K. Craig Kent, Fitchburg, WI (US); Shaoqin Gong, Middleton, WI (US); Xudong Shi, Madison, WI (US); Guojun Chen, Madison, WI (US); Lian-Wang Guo, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/674,293

(22) Filed: Aug. 10, 2017

(65) Prior Publication Data

US 2018/0042844 A1 Feb. 15, 2018

Related U.S. Application Data

(60) Provisional application No. 62/375,387, filed on Aug. 15, 2016.

(51) Int. Cl.
*A61K 9/107* (2006.01)
*A61K 31/436* (2006.01)
(Continued)

(52) U.S. Cl.
CPC .............. *A61K 9/1075* (2013.01); *A61K 9/06* (2013.01); *A61K 31/436* (2013.01); *A61K 47/34* (2013.01); *A61K 9/5146* (2013.01); *A61K 9/5153* (2013.01)

(58) Field of Classification Search
CPC .... A61K 9/5146; A61K 9/5153; A61K 47/34; A61K 9/06; A61K 31/436; A61K 9/1075
See application file for complete search history.

(56) References Cited

U.S. PATENT DOCUMENTS

| | | | | |
|---|---|---|---|---|
| 5,833,647 | A * | 11/1998 | Edwards | A61K 9/0009 604/22 |
| 2003/0003074 | A1 * | 1/2003 | Zentner | A61K 9/0024 424/85.2 |

(Continued)

OTHER PUBLICATIONS

Wang et al., "Synthesis and Characterization of star Poly(ε-caprolactone)-b-Poly(ethylene glycol) and poly(L-Lactide)-b-Poly(ethylene glycol) Copolymer: Evaluation as Drug Delivery Carriers", Bioconjugate Chem., 2008, 19, 1423-1429 (Year: 2008).*

(Continued)

*Primary Examiner* — Jianfeng Song
(74) *Attorney, Agent, or Firm* — Thomas|Horstemeyer, LLP

(57) ABSTRACT

The present technology provide compositions that are drug delivery systems for the sustained release of anti-stenotic drugs for the treatment and prevention of occlusion of blood vessels, particularly after perivascular surgery. The compositions include a hydrogel, unimolecular micelles dispersed within the hydrogel, and an effective amount of anti-stenotic drug dispersed within the unimolecular micelle. The hydrogel may be a di-or tri-block copolymer comprising one block of poly(ethylene glycol) (PEG) and one or two blocks of poly(lactic-co-glycolic acid) (PLGA). The unimolecular micelle may include three domains: a dendritic polymer core, hydrophobic block polymers (e.g., PVL, PVCL, and/or PCL) attached to the core and PEG attached to the hydrophobic block polymers.

7 Claims, 3 Drawing Sheets

Fig. 3. Rapamycin release rates.

| Delivery method | Release time |
|---|---|
| (---) Pluronic gel | 3 days |
| (···) Triblock gel | 30 days |
| (—) Unimol.NP alone | 60 days |
| (—) Unimol.NP/Triblock gel | >90 days |

(51) Int. Cl.
      A61K 47/34    (2017.01)
      A61K 9/06     (2006.01)
      A61K 9/51     (2006.01)

(56) References Cited

U.S. PATENT DOCUMENTS

2011/0166417 A1*  7/2011  Lin .................... F01N 13/08
                                                    600/104
2014/0178474 A1*  6/2014  Bredehorst ........ A61K 39/3955
                                                    424/484

OTHER PUBLICATIONS

Zeng et al., "Synthesis and Characterization of Six-Arm Star Poly(σ-valerolactone)-block-Methoxy Poly(ethylene glycol) Copolymers", Biomacromolecules, 2005, 6 (4), pp. 2140-2149 (Year: 2005).*
Brinkman, et al., "Aminoflavone-Loaded EGFR-Targeted Unimolecular Micelle Nanoparticles Exhibit Anti-Cancer Effects in Triple Negative Breast Cancer," Biomaterials, 2016, 101, pp. 20-31.
Chaudhary, et al., "Periadventitial Drug Delivery for the Prevention of Intimal Hyperplasia Following Open Surgery," Journal of Controlled Release, 2016, 233, pp. 174-80.
Chen, et al., "Abstract 160: Perivascular Administration of Rapamycin Through Nanoparticles Prolongs Inhibition of Arterial Restenosis," Arteriosclerosis, Thrombosis, and Vascular Biology, 2014, 34, A160.
Chen, et al., "Multi-Functional Self-Fluorescent Unimolecular Micelles for Tumor-Targeted Drug Delivery and Bioimaging," Biomaterials, 2015, 47, pp. 41-50.
Cheng, et al., "Dendritic Cell Function in Transplantation Arteriosclerosis is Regulated by Heme Oxygenase 1," Circulation Research, 2010, 106, pp. 1656-1666.
Goel et al., "High-Throughput Screening Identifies Idarubicin as a Preferential Inhibitor of Smooth Muscle Versus Endothelial Cell Proliferation," PloS One, 2014, 9, e89349.
Goel, et al., "Mechanisms of Post-Intervention Arterial Remodelling," Cardiovascular Research, 2012, 96, pp. 363-371.
Guo, et al., "Halofuginone Stimulates Adaptive Remodeling and Preserves Re-Endothelialization in Balloon-Injured Rat Carotid Arteries," Circulation: Cardiovascular Interventions, 2014, 7, pp. 594-601.
Guo, et al., Image-Guided and Tumor-Targeted Drug Delivery with Radiolabeled Unimolecular Micelles, Biomaterials, 2013, 34, pp. 8323-8332.
Hollenbeck, et al., "Stem Cell Factor and C-Kit are Expressed by and May Affect Vascular SMCS Through an Autocrine Pathway," Journal of Surgical Research, 2004, 120, pp. 288-294.
Jaskula-Sztul, et al., "Thailandepsin A-Loaded and Octreotide-Functionalized Unimolecular Micelles for Targeted Neuroendocrine Cancer Therapy," Biomaterials, 2016, 91, pp. 1-10.
Kundi, et al., "Arterial Gene Transfer of the TGF-Beta Signalling Protein Smad3 Induces Adaptive Remodelling Following Angioplasty: A Role for CTGF," Cardiovascular Research, 2009, 84, pp. 326-335.
Prabaharan, et al., "Amphiphilic Multi-Arm-Block Copolymer Conjugated with Doxorubicin Via pH-Sensitive Hydrazone Bond for Tumor-Targeted Drug Delivery," Biomaterials, 2009, 30, pp. 5757-5766.
Prabaharan, et al., "Folate-Conjugated Amphiphilic Hyperbranched Block Copolymers Based on Boltorn H40, Poly(L-Lactide) and Poly(Ethylene Glycol) for Tumor-Targeted Drug Delivery," Biomaterials, 2009, 30, pp. 3009-3019.
Schubl, et al., "Upregulation of Protein Kinase C-Delta in Vascular Smooth Muscle Cells Promotes Inflammation in Abdominal Aortic Aneurysm," Journal of Surgical Research, 2009, 153, pp. 181-187.
Seedial, et al., "Local Drug Delivery to Prevent Restenosis," Journal of Vascular Surgery, 2013, 57, pp. 1403-1414.
Shi, et al., "Periadventitial Application of Rapamycin-Loaded Nanoparticles Produces Sustained Inhibition of Vascular Restenosis," PloS One, 2014, 9, 2, e89227.
Shi, et al., "TGF-beta/Smad3 Inhibit Vascular Smooth Muscle Cell Apoptosis Through an Autocrine Signaling Mechanism Involving VEGF-A," Cell Death and Disease, 2014, 5, e1317.
Shi, et al., "TGF-Beta/Smad3 Stimulates Stem Cell/Developmental Gene Expression and Vascular Smooth Muscle Cell De-Differentiation," PloS One, 2014, 9, e93995.
Si, et al., "Protein Kinase C-Delta Mediates Adventitial Cell Migration Through Regulation of Monocyte Chemoattractant Protein-1 Expression in a Rat Angioplasty Model," Arteriosclerosis, Thrombosis, and Vascular Biology, 2012, 32, pp. 943-954.
Suwanabol, et al., "TGF-beta and Restenosis Revisited: A Smad Link," Journal of Surgical Research, 2011, 167, pp. 287-297.
Takayama, et al., "A Murine Model of Arterial Restenosis: Technical Aspects of Femoral Wire Injury," Journal of Visualized Experiments, 2015, 97, 52561.
Tsai, et al., "TGF-beta Through Smad3 Signaling Stimulates Vascular Smooth Muscle Cell Proliferation and Neointimal Formation," American Journal of Physiology:Heart and Circulatory Physiology, 2009, 297, pp. H540-549.
Wang, et al., "Multifunctional Chondroitin Sulphate for Cartilage Tissue-Biomaterial Integration," Nature Materials, 2007, 6, pp. 385-392.
Wang, et al., "BET Bromodomain Blockade Mitigates Intimal Hyperplasia in Rat Carotid Arteries," EBioMedicine, 2015, 2, pp. 1650-1661.
Xiao, et al., "Multifunctional Unimolecular Micelles for Cancer-Targeted Drug Delivery and Positron Emission Tomography Imaging," Biomaterials, 2012, 33, pp. 3071-3082.
Xu, et al., "Aptamer-Conjugated and Doxorubicin-Loaded Unimolecular Micelles for Targeted Therapy of Prostate Cancer," Biomaterials, 2013, 34, pp. 5244-5253.
Xu, et al., "Octreotide-Functionalized and Resveratrol-Loaded Unimolecular Micelles for Targeted Neuroendocrine Cancer Therapy," Nanoscale, 2013, 5, pp. 9924-9933.
Yang, et al., "Tumor-Targeting, pH-Responsive, and Stable Unimolecular Micelles as Drug Nanocarriers for Targeted Cancer Therapy," Bioconjugate Chemistry, 2010, 21, pp. 496-504.
Yu, et al., "A Rapamycin-Releasing Perivascular Polymeric Sheath Produces Highly Effective Inhibition of Intimal Hyperplasia," Journal of Controlled Release, 2014, 191, pp. 47-53.

* cited by examiner

PERIVASCULAR DRUG DELIVERY SYSTEM

CROSS-REFERENCE TO RELATED APPLICATIONS

This application claims priority to U.S. Provisional Patent Application No. 62/375,387, filed on Aug. 15, 2016, the entire contents of which are incorporated herein by reference.

GOVERNMENT RIGHTS

This invention was made with government support under HL068673 and CA166178 awarded by the National Institutes of Health. The government has certain rights in the invention.

FIELD

The present disclosure relates generally to perivascular drug delivery systems and methods of preparing and using such systems. The compositions of such systems include a hydrogel, unimolecular micelle and anti-stenotic drug(s).

BACKGROUND

Each year over a million patients in the US are treated with vascular surgical procedures for flow-limiting atherosclerosis or for hemodialysis access. Although initially successful, a large proportion of these reconstructions eventually fail due to intimal hyperplasia (IH). IH can result from injury that occurs at the time of arterial reconstruction, for example, manipulation of a vein being prepared for bypass. Alterations of hemodynamics can provide a more persistent stimulus for IH. An example of this is the exposure of a vein graft to arterial pressures and subsequent arteriolization of the vein. The development of recurrent disease leads to the narrowing of the new conduit with the eventual development of stenosis or occlusion.

IH remains a major cause of poor patient outcomes after surgical revascularization to treat atherosclerosis. A multitude of drugs have been shown to prevent the development of IH. Moreover, endovascular drug delivery following angioplasty and stenting has been achieved with a marked diminution in the incidence of restenosis. Despite advances in endovascular drug delivery, there is currently no clinically available method of periadventitial drug delivery suitable for open vascular reconstructions.

SUMMARY

The present technology provides compositions that constitute drug delivery systems for anti-stenotic drugs that may be applied to the periadventitial surface (outer surface) of an artery or vein. The compositions include a hydrogel, unimolecular nanoparticles such as unimolecular micelles dispersed within the hydrogel, and an effective amount of anti-stenotic drug dispersed within the unimolecular micelle. The hydrogel may be a di-or tri-block copolymer comprising one block of poly(ethylene glycol) (PEG) and one or two blocks of poly(lactic-co-glycolic acid) (PLGA), wherein the di- or tri-block copolymer has a molecular weight of about 1,500 to about 5,000 Daltons (Da). The unimolecular nanoparticle or micelle typically includes three domains: a dendritic polymer having a molecular weight of 500 to 10,000 Da and terminating in hydroxyl, amino or carboxylic acid groups; hydrophobic block polymers attached to at least a majority of the terminating groups of the dendritic polymer (i.e., attached to the hydroxyl, amino, or carboxylic acid groups), wherein the hydrophobic block polymers have a molecular weight from 1,000 to 5,000 Da and which are selected from the group consisting of poly(valerolactone) (PVL), poly(valerolactone-co-lactic acid) (PVCL), and poly(caprolactone) (PCL), and PEG attached to the hydrophobic polymer block and terminating in OH, O-alkyl, $NH_2$, or biotin, and having a molecular weight of 1,000 to 15,000 Da. The unimolecular micelles are loaded with anti-stenotic drugs such as rapamycin, resveratrol, halofuginone, idarubicin, (S)-tert-butyl 2-(4-(4-chlorophenyl)-2,3,9-trimethyl-6H-thieno[3,2-f][1,2,4]triazolo[4,3-α][1,4]diazepin-6-yl) acetate (JQ1), 1-[5-(4-Amino-7-methyl-7H-pyrrolo[2,3-d]pyrimidin-5-yl)indolin-1-yl]-2-(3-trifluoromethylphenyl)-ethanone (GSK2606414) and a combination of any two or more thereof.

Compositions of the present technology may provide one or more of the following advantages. Since the anti-stenotic drug may be applied to the adventitia, away from the endothelial layer, there is diminished impairment of endothelial healing. The drug delivery compositions are not bulky and have minimal effect on the hemodynamics of the treated arterial wall. The compositions also allow for sustained and steady release of anti-stenotic drugs where the stimuli for IH following arterial reconstruction is often persistent. In addition, the polymeric degradation products are minimal and unlikely to produce perivascular inflammation or constrictive remodeling.

DETAILED DESCRIPTION

Figure 1:
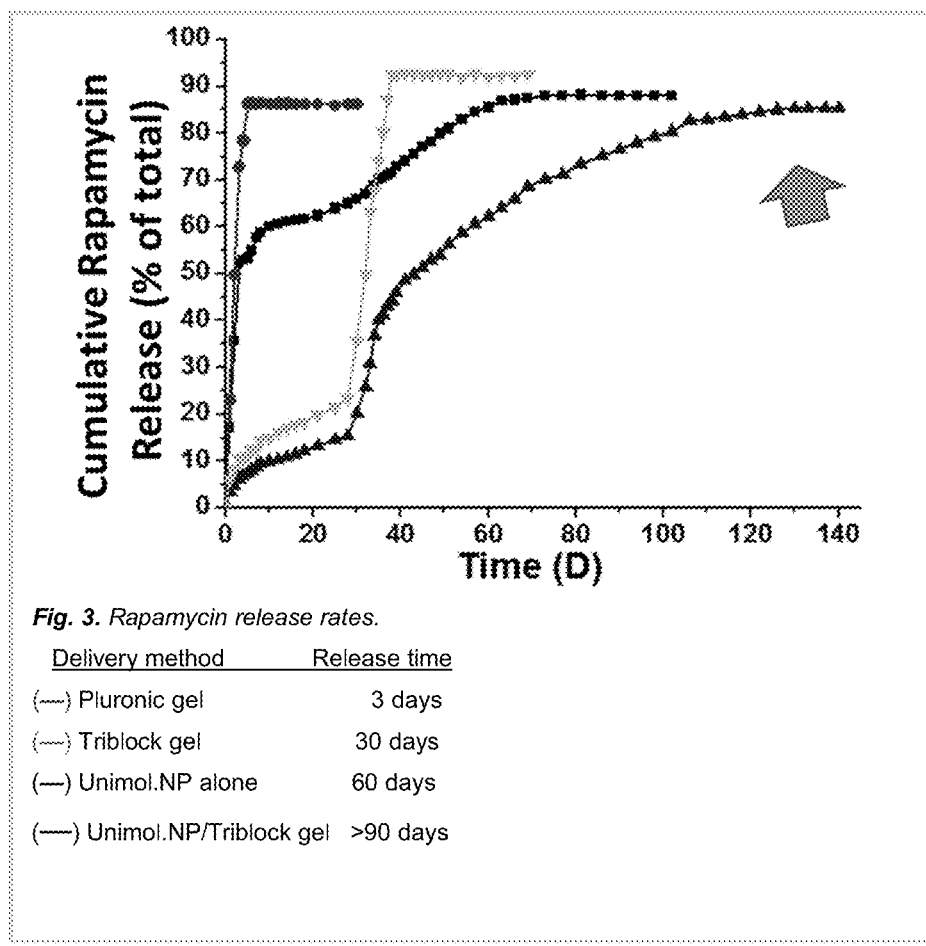
FIG. 1 shows cumulative rapamycin release over time from an illustrative embodiment of the present technology (unimolecular micelle nanoparticles (NPS) in PLGA-PEG-PLGA triblock thermosensitive gel (▲) and comparative technologies: Pluronic gel (●), NPs alone (■), and PLGA-PEG-PLGA triblock thermosensitive gel alone (▼).

The following terms are used throughout as defined below. All other terms and phrases used herein have their ordinary meanings as one of skill in the art would understand.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, "alkyl groups" include straight chain and branched chain alkyl groups having 1, 2, 3, 4, 5, or 6 carbon atoms. Examples of straight chain alkyl groups include groups such as methyl, ethyl, n-propyl, n-butyl, n-pentyl, and n-hexyl. Examples of branched alkyl groups include, but are not limited to, isopropyl, iso-butyl, sec-butyl, tert-butyl, neopentyl, isopentyl, and 2,2-dimethylpropyl groups. Alkyl groups are unsubstituted unless otherwise indicated.

A "drug delivery system" or "drug delivery composition having thermal gelation properties" refers to a polymer solution that contains a drug or combination of drugs, where the drug(s) per se can be either dissolved or colloidal), suitable for administration to a warm-blooded animal, which forms a gelled drug depot when the temperature is raised to or above the gelation temperature of the block copolymer.

A "gel" refers to the semi-solid phase that spontaneously occurs as the temperature of the "polymer solution" or "drug delivery system" is raised to or above the gelation temperature of the block copolymer.

An "aqueous polymer composition" refers to either a drug delivery system or a gel comprised of the water phase having uniformly contained therein a drug or drug combination and the biodegradable block copolymer described herein. At temperatures below the gelation temperature the copolymer may be soluble in the water phase and the composition will be a solution. At temperatures at or above the gelation temperature the copolymer will solidify to form a gel with the water phase and the composition will be a gel or semi-solid.

The term "biodegradable" means that the block copolymer can chemically break down or degrade within the body to form nontoxic components under physiological conditions. The rate of degradation can be the same or different from the rate of drug release.

As used herein, the term "dendritic polymers" refers to non-linear polymers having a plurality of branching chains, and a large number of end groups. Dendritic polymers include dendrimers, which have star-like branched topologies, and hyperbranched polymers, which have irregular branched structures. A dendritic polymer includes an initiator moiety having at least two (and potentially three or four) functional groups to which repeating layers of multifunctional monomers are attached. The outermost layer is terminated by functional groups known as end groups. The initiator is termed generation 0 and each layer is numbered in sequence: 1, 2, 3, 4, and so forth. As descried below, the dendritic polymers of the present technology form the core of the unimolecular micelle. Suitable dendritic polymers include but are not limited to polyester hyperbranched polymers (e.g., Boltorn H40) and polyamidoamine dendrimers (e.g., PAMAM).

A "polymer solution," "aqueous solution" and the like, when used in reference to a biodegradable block copolymer contained in such solution, refers to a water-based solution having the recited block copolymer dissolved therein at a functional concentration, and maintained at a temperature below the gelation temperature of the block copolymer. "Thermal gelation" is the phenomena whereby a solution of a block copolymer spontaneously increases in viscosity, and in many instances transforms into a semisolid gel, as the temperature of the solution is increased above the gelation temperature of the copolymer. For example, the term "gel" includes both the semisolid gel state and the high viscosity state that exists above the gelation temperature. When cooled below the gelation temperature, the gel spontaneously reverses to reform the lower viscosity solution. Cycling between the solution and the gel may be repeated ad infinitum because the sol/gel transition does not involve any change in the chemical composition of the polymer system. Interactions to create the gel are physical in nature and do not involve the formation or breaking of covalent bonds.

"Gelation temperature" refers to the temperature at which a block copolymer undergoes thermal gelation, i.e. the temperature below which the block copolymer is soluble in water and above which the block copolymer undergoes phase transition to increase in viscosity or to form a semi-solid gel. The terms "gelation temperature," "thermal gelation temperature," and similar terms can be used interchangeably, as would be readily recognized by one of skill in the art.

A "hydrophobic drug" refers to a water insoluble drug. A water insoluble drug has a solubility of less than 0.1 mg/mL in distilled water at 25° C. Within the context of this disclosure, a "slightly soluble drug" has a solubility of about 1-10 mg/mL and a "very slightly soluble drug" has a solubility of about 0.1-1 mg/mL. These terms are well-known to those of skill in the art. See, e.g., Martin (ed.), *Physical Pharmacy*, Fourth Edition, page 213 (Lea and Febiger 1993).

"Molecular weight" as used herein with respect to polymers refers to weight average molecular weights ($M_w$) and can be determined by techniques well known in the art including gel permeation chromatography (GPC). GPC analysis can be performed, for example, on a Styragel HR-3 column calibrated with PEG using RI detection and chloroform as the eluent.

A "stable thermogel," or "thermosensitive hydrogel" as used herein refers to a composition that forms a stable non-flowing hydrogel at above about 20° C. and is a free-flowing solution at less than about 10° C.

A "unimolecular micelle" as used herein refers to a micelle formed from a single large polymer rather than a plurality of polymers. In the present technology, the polymer of the unimolecular micelle is a multi-arm star-like amphiphilic block copolymer. It includes a core dendritic polymer that terminates in a hydrophobic polymer blocks, which in turn terminate in hydrophilic polymer blocks. Each hydrophilic blocks may terminate in a water solubilizing groups such as amines, alcohols, carboxylic acids or the like or in a $C_{1-4}$ alkyl ether.

The present technology provides pharmaceutical compositions and medicaments comprising any of one of the embodiments of the drug delivery systems disclosed herein and a pharmaceutically acceptable carrier or one or more excipients. The compositions may be used in the methods and treatments described herein. The pharmaceutical composition may include an effective amount of any of one of the embodiments of the compositions disclosed herein. In any of the above embodiments, the effective amount may be determined in relation to a subject. "Effective amount" refers to the amount of compound or composition required to produce a desired effect. One example of an effective amount includes amounts or dosages that yield acceptable toxicity and bioavailability levels for therapeutic (pharmaceutical) use including, but not limited to, the inhibition (i.e., slowing, halting or reversing) or prevention of stenosis in a blood vessel. As used herein, a "subject" or "patient" is a mammal, such as a cat, dog, rodent or primate. Typically the subject is a human, and, preferably, a human at risk for or suffering from stenosis due to, e.g., a perivascular graft. The term "subject" and "patient" can be used interchangeably.

In one aspect the present technology provides a drug delivery system for the prevention of stenosis in blood vessels, particularly veins. The drug delivery systems include compositions comprising a hydrogel, unimolecular micelles dispersed within the hydrogel, and an effective amount of anti-stenotic drug dispersed within the unimolecular micelle. As used herein, "dispersed" means distributed, in a generally uniform or in a non-uniform fashion. In some embodiments, the unimolcular micelles are dispersed in a generally uniform fashion within the hydrogel. However, it will be understood that hydrogels with a non-uniform distribution of unimolecular micelles, especially those with small variations in concentration of the micelles are within the scope of the present technology. The anti-stenotic drug may also be non-uniformly distributed within the unimolecular micelles as described below.

The hydrogel of the present technology is a di-or tri-block copolymer comprising one block of poly(ethylene glycol) (PEG) and one or two blocks of poly(lactic-co-glycolic acid) (PLGA). In some embodiments the hydrogel is PLGA-PEG or PLGA-PEG-PLGA. In some embodiments, the di- or tri-block copolymer has a molecular weight of 1,500 to 5,000 Da (i.e., 1.5 kDa to 5 kDa). In certain embodiments, the hydrogel copolymer has a molecular weight of 1.5 kDa, 2 kDa, 2.5 kDa, 3 kDa, 3.5 kDa, 4 kDa, 4.5 kDa, 5 kDa or a range between and including any two of the foregoing values, e.g., 3 kDa to 5 kDa.

The PLGA block of the hydrogel copolymers herein can be synthesized from a variety of monomers such as D,L-lactide, D-lactide, L-lactide, D,L-lactic acid, D-lactic acid, L-lactic acid, glycolide, and/or glycolic acid. The molecular weight of PLGA blocks in the hydrogel copolymers may be from about 800 Da to about 2000 Da. For example the molecular weight of each PLGA block may be about 800 Da, about 900 Da, about 1000 Da, about 1100 Da, about 1200 Da, about 1300 Da, about 1400 Da, about 1500 Da, about 1600 Da, about 1700 Da, about 1800 Da, about 1900 Da, about 2000 Da, or a range between and including any two of these values. Each PLGA block may include from 1:4 to 4:1 lactic acid to glycolic acid residues on a molar basis. For example, each PLGA block may include 1:4, 1:3, 1:2, 1:1, 2:1, 3:1, or 4:1 molar ratios of lactic acid to glycolic acid residues or a range of ratios between and including any two of the foregoing values, such as from 2:1 to 4:1.

As used herein, PEG may also be referred to as poly(ethylene oxide) (PEO) or poly(oxyethylene). The molecular weight (in daltons) of PEG in the di- and tri-block hydrogel copolymers described herein may be about 700 Da to about 2,000 Da. For example, the molecular weight of PEG in the copolymers may be about 700 Da, about 800 Da, about 900 Da, about 1,000 Da, about 1,100 Da, about 1,200 Da, about 1,300 Da, about 1,400 Da, about 1,500 Da, about 1,600 Da, about 1,700 Da, about 1,800 Da, about 1,900 Da, about 2,000 Da, or a range between and including any two of these values, such as about 1000 Da to about 2000 Da, or about 900 Da to about 1200 Da.

In some embodiments, the hydrogel is a thermogel that can exhibit water solubility at low temperatures (e.g., below about 10-20° C.) and undergo reversible thermal gelation at higher temperatures, such as mammalian physiological body temperatures. For example, the PLGA-PEG-PLGA copolymer may have a PEG content of about 15-50 wt % (e.g., about 20 to about 40 wt %), a total PLGA content of about 50-85 wt % (e.g., about 60 to about 80 wt %), a lactic acid content of about 60-85 mole percent, and a glycolic acid content of about 15-40 mole percent, where the polymer is water soluble below the gelation temperature (e.g., about 10-20° C.) and forms a stable thermogel above the gelation temperature (e.g., above about 20° C.).

The triblock copolymer can be synthesized by ring opening polymerization or condensation polymerization, for example, as described by U.S. Pat. No. 6,004,573 (Rathi et al.) and U.S. Pat. No. 7,135,190 (Piao et al.). Suitable polymers, such as PLGA-b-PEG-b-PLGA (1.5k-1k-1.5k), can also be obtained commercially from suppliers such as Polyscitech (West Lafayette, Ind.; http://www.polyscitech.com).

The unimolecular micelle of the present technology includes three distinct domains: a dendritic polymer having a molecular weight of 500 to 10,000 Da and terminating in amino, hydroxyl or carboxylic acid groups; hydrophobic block polymers attached to at least a majority of the terminal amino, hydroxyl or carboxylic acid groups of the dendritic polymer, wherein the hydrophobic block polymers have a molecular weight from 1,000 to 5,000 Da and which are biodegradable and biocompatible such as polyesters. The polyesters may be selected from the group consisting of poly(valerolactone) (PVL), poly(valerolactone-co-lactic acid) (PVCL), and poly(caprolactone) (PCL), and PEG attached to the hydrophobic polymer blocks and terminating in OH, O-alkyl, $NH_2$, or biotin, and having a molecular weight of 1,000 to 15,000 Da.

The core of the unimolecular micelle may be a dendrimer such as a poly(amido-amine) (PAMAM) dendrimer having from 3 to 7 generations (e.g., 3, 4, 5, 6, or 7 generations or a range between and including any two of the foregoing values) or a hyperbranched polymer such as a polyester hyperbranched polymer (e.g., Baltorn H30 and H40). PAMAM will be understood to refer to a polymer having a $C_2$-$C_4$ α, ω-diamine initiator and $C_3$-$C_4$ acrylate and diamine building blocks for each subsequent generation. Typically the building blocks are $C_2$ 1,2-diamines and $C_3$ acrylates (not counting the methyl ester carbon, which serves as a temporary protecting group). In some embodiments, the PAMAM dendrimer has from 3 to 4 generations. Although not every arm of the dendritic polymer must terminate in amino, hydroxyl or carboxylic acid groups, the majority of arms of the dendritic polymer do, e.g., more than 50%, more than 60%, more than 70%, more than 80% or more than 90% of arms of the dendritic polymer terminate in amino or hydroxyl groups. In some embodiments, e.g., where the dendritic polymer is PAMAM, all of the arms terminate in amino groups or hydroxyl groups.

The hydrophobic block polymers of the unimolecular micelle link the core dendritic polymer to the outer PEG blocks. In some embodiments, the hydrophobic polymer blocks are PCL or PVCL. In others they are PVL. In certain embodiments, the molecular weight of each hydrophobic polymer block is about 1,000 to about 5,000 Da; in others it is about 1,500 to about 4,000 Da. Suitable molecular weights include about 1,000, about 1,500, about 2,000, about 2,500, about 3,000, about 3,500, about 4,000, about 4,500, about 5,000 or a range between and including any two of the foregoing values.

PEG is a hydrophilic polymer that forms the outer layer of the unimolecular micelle. Each arm of the PEG terminates in various groups such as OH, O-alkyl, $NH_2$, or biotin or a combination of two or more thereof. In some embodiments the PEG terminates in OH or O-alkyl, and in still others the PEG terminates in in an $OC_{1-3}$ alkyl group. Typically each arm of the PEG has 23 to 340 repeat units or a molecular weight of about 1,000 to about 15,000 Da. Suitable molecular weights for each PEG block of the unimolecular micelle include about 1,000, about 1,500, about 2,000, about 2,500, about 3,000, about 4,000, about 5,0000, about 7,500, about 10,000, or about 15,000 Da, or a range between and including any two of the foregoing values. In some embodiments, the unimolecular micelle comprises PAMAM-PVL-PEG with a molecular weight of 100,000 to 350,000 Da.

The unimolecular nanoparticles or micelles may be prepared using standard techniques. For example, a dendritic polymer in which most or all of the surface arms terminate in amino, hydroxyl, or carboxylic acid groups may be conjugated to the hydrophobic block polymers via amide, ester, or ether groups. Typically, ester and amide linkages are used for ease of formation. Likewise, the PEG blocks may be attached to the hydrophobic block polymers via ester or ether groups. In some embodiments, the PEG have a hydroxy group on one end and an alkoxy or carbonylalkoxy on the other. Standard coupling conditions such as the use of tin catalysis or coupling agents or active esters may be used to form the ester or amide bonds.

Anti-stenotic drugs that inhibit or prevent stenosis of a blood vessel may be used in the present drug delivery systems. Typically, the anti-stenotic drugs are hydrophobic drugs. Suitable anti-stenotic drugs include, for example, rapamycin, resveratrol, halofuginone, idarubicin, (S)-(+)-tert-butyl 2-(4-(4-chlorophenyl)-2,3,9-trimethyl-6H-thieno [3,2-f][1,2,4]triazolo[4,3 -α][1,4]diazepin-6-yl)acetate (JQ1), 1[5-(4-Amino-7-methyl-7H-pyrrolo[2,3-d]pyrimidin-5-yl)indolin-1-yl]-2-(3-trifluoromethylphenyl)ethanone (GSK2606414) and a combination of any two or more thereof. In some embodiments, the anti-stenotic drug is rapamycin. The loading of the anti-stenotic drug is typically from about 1 to about 35 wt % of the unimolecular micelles (dry weight), or in some embodiments about 5 wt % to about 30 wt % or even about 10 wt % or 15 wt % to about 25 wt % or about 30 wt %. Exemplary loading amounts of the anti-stenotic drug include about 1 wt %, about 2 wt %, about 3 wt %, about 4 wt %, about 5 wt %, about 10 wt %, about 15 wt %, about 20 wt %, about 25 wt %, about 30 wt % or about 35 wt % of the unimolecular micelles or a range between and including any two of the forgoing values.

It will be understood that any of the herein-disclosed embodiments of hydrogels and drug-loaded unimolecular micelles may be combined. Thus for example, the present technology provides a composition including a hydrogel, unimolecular micelles dispersed within the hydrogel, and an anti-stenotic effective amount of rapamycin dispersed within the unimolecular micelle, wherein the hydrogel is a PLGA-b-PEG-b-PLGA copolymer having a molecular weight of about 2,500 to about 3,500 Da; and the unimolecular micelle comprises PAMAM-PVL-PEG-O($C_{1-3}$ alkyl) and has a molecular weight of about 100,000 to about 350,000 Da, wherein the PAMAM is a 3- or 4-generation dendrimer.

The present drug delivery compositions provides for sustained release of anti-stenotic drugs directly to the blood vessel at risk of developing, e.g., IH. Thus, in another aspect, the present technology provides methods of inhibiting or preventing stenosis of a blood vessel by administering the drug delivery system/composition as described herein to the blood vessel at risk of stenosing such as a vein. The administering step may include applying the drug delivery system/composition to the outside of the blood vessel, or directly "painting" unimolecular micelles onto the vessel. The hydrogel of the invention is typically thermosensitive; it is relatively free flowing at room temperature or below, but will gel once exposed to body temperature. While not wishing to be bound by theory, it is believed that the unimolecular micelles act as a reservoir of anti-stenotic drug within the hydrogel. The anti-stenotic drugs are presumed to partition into the hydrophobic core of the unimolecular micelle among the dendritic polymer and hydrophobic polymer blocks rather than among the outer PEG chains. In some embodiments, once the hydrogel breaks down, the unimolecular micelles may remain in the area of the injured vessel, continuing to release drug until they also break down. It is believed that light scar tissue may confine the unimolecular micelles after the hydrogel breaks down.

The compositions described herein can be formulated for various routes of administration, for example, by parenteral, rectal, nasal, vaginal administration, or via implanted reservoir. Parenteral or systemic administration includes, but is not limited to, subcutaneous, intravenous, intraperitoneal, and intramuscular injections. The following dosage forms are given by way of example and should not be construed as limiting the instant present technology.

Injectable dosage forms generally include solutions or aqueous suspensions which may be prepared using a suitable dispersant or wetting agent and a suspending agent so long as such agents do not interfere with formation of the micelles described herein. Injectable forms may be prepared with acceptable solvents or vehicles including, but not limited to sterilized water, Ringer's solution, 5% dextrose, or an isotonic aqueous saline solution.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

Specific dosages may be adjusted depending on conditions of disease, the age, body weight, general health conditions, sex, and diet of the subject, dose intervals, administration routes, excretion rate, and combinations of drug conjugates. Any of the above dosage forms containing effective amounts are well within the bounds of routine experimentation and therefore, well within the scope of the instant present technology. By way of example only, such dosages may be used to administer effective amounts of the antistenotic drugs to the patient and may include about 0.1 mg/kg, about 0.2 mg/kg, about 0.3 mg/kg, about 0.4 mg/kg, about 0.5 mg/kg, about 0.75 mg/kg, about 1 mg/kg, about 1.25 mg/kg, about 1.5 mg/kg, or a range between and including any two of the forgoing values. Such amounts may be administered parenterally as described herein and may take place over a period of time including but not limited to 5 minutes, 10 minutes, 20 minutes, 30 minutes, 45 minutes, 1 hour, 2 hours, 3 hours, 5 hours, 10 hours, 12, hours, 15 hours, 20 hours, 24 hours or a range between and including any of the foregoing values. The frequency of administration may vary, for example, once per day, per 2 days, per 3 days, per week, per 10 days, per 2 weeks, or a range between and including any of the foregoing frequencies. Alternatively, the compositions may be administered once per day on 2, 3, 4, 5, 6 or 7 consecutive days. A complete regimen may thus be completed in only a few days or over the course of 1, 2, 3, 4 or more weeks.

In another aspect, the present technology provides kits including the components needed to prepare any of the compositions described herein. For example, a kit may include a package containing a hydrogel, a package containing unimolecular micelles with an effective amount of anti-stenotic drug dispersed within the unimolecular micelles and directions for use of the kit. In such kits, the hydrogel may be a di-or tri-block copolymer comprising one block of poly(ethylene glycol) (PEG) and one or two blocks of poly(lactic-co-glycolic acid) (PLGA), wherein the di- or tri-block copolymer has a molecular weight of about 2,000 to about 5,000 Da. The unimolecular micelle may include a dendritic polymer having a molecular weight of 500 to 10,000 Da and terminating in hydroxyl, amino or carboxylic acid groups, hydrophobic block polymers attached to at least a majority of the terminal groups of the dendritic polymer (i.e., the amine and/or hydroxyl groups), wherein the hydrophobic block polymers have a molecular weight from about 1,000 to about 5,000 Da and which are selected from the group consisting of PVL, PVCL, and PCL, and poly(ethylene glycol) attached to the hydrophobic polymer block and terminating in OH, O-alkyl, $NH_2$, or biotin, and having a molecular weight of about 1,000 to about 15,000 Da. The anti-stenotic drug may be selected from the group consisting of rapamycin, resveratrol, halofuginone, idarubicin, (S)-tert-butyl 2-(4-(4-chlorophenyl)-2,3,9-trimethyl-6H-thieno[3,2-f][1,2,4]triazolo[4,3 -α][1,4]diazepin-6-yl)acetate, 1-[5-(4-Amino-7-methyl-7H-pyrrolo[2,3-d]pyrimidin-5-yl)indolin-1-yl]-2-(3-trifluoromethylphenyl)ethanone, and a combination of any two or more thereof. However, it will be understood that the kit may include any of the hydrogels and drug-loaded unimolecular micelles described herein. In some embodiments the kits may include separate packages for the unimolecular micelles and anti-stenotic drug(s). The present kits allow the user to prepare the drug delivery composition described herein by dispersing the drug-loaded molecular micelles in the hydrogel.

The examples herein are provided to illustrate advantages of the present technology and to further assist a person of ordinary skill in the art with preparing or using the micelle compositions of the present technology. To the extent that the compositions include ionizable components, salts such as pharmaceutically acceptable salts of such components may also be used. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Example 1

Synthesis of Preparation of Rapamycin-Loaded Unimolecular Micelle

Synthesis of PAMAM-PVL. A 50 ml two-neck flask equipped with an argon gas inlet was charged with a 4-generation (64 arms) polyamidoamine dendrimer having ethanol surface groups (PAMAM-OH) and placed in an oil bath. Valerolactone (VL) was slowly introduced and a catalytic amount of $Sn(Oct)_2$ ($[Sn(Oct)_2]/[VL]=1/1000$ mol/mol) was added subsequently. The reaction was stirred at 120° C. for 24 h. The resulting mixture was dissolved in THF and the solution was added dropwise into methanol to yield a pale yellow precipitate. The product PAMAM-PVL was dried under vacuum. The PVL weight average molecular weight was about 2,600 Da.

Synthesis of PAMAM-PVL-PEG. PAMAM-PVL as prepared above and $CH_3O$-PEG-COOH (about 5,000 Da) were dissolved in 10 mL of anhydrous dimethylsulfoxide (DMSO), in present of dicyclohexylcarbodiimide and dimethylamino pyridine as catalysts. The reaction was carried out at room temperature for 48 h. After the by-product, dicyclohexylcarbodiurea, was removed by filtration, the solution was added dropwise into cold diethyl ether. The precipitate was re-dispersed in deionized (DI) water and the impurities were removed by dialysis against DI water for 48 h using a cellulose membrane (molecular weight cut-off, 15 kDa). The product was dried by lyophilization.

Preparation of rapamycin-loaded unimolecular micelle nanoparticles (NPs). Rapamycin-loaded unimolecular micelles were prepared using the membrane dialysis method. PAMAM-PVL-PEG-OMe and rapamycin were dissolved in 3 mL of DMF. 9 mL of DI water was added dropwise into the above solution. Thereafter, the solution was dialyzed by a cellulose membrane (molecular weight cut-off, 15 kDa) for 48 h to remove the DMF and free drug. The final product was dried by lyophilization.

Example 2

Preparation of Triblock Gel (PLGA-PEG-PLGA)

OH-PEG-OH (Mw=1 kDa) was dried in a three-necked flask under vacuum at 120° C. for 2 h. Lactide (LA) and glycolide (GA) (molar ratio of LA/GA was 3:1) were added to the flask and dried under vacuum at 70° C. for 30 min. Thereafter, a catalyst amount of $Sn(Oct)_2$ ($[Sn(Oct)_2]/([LA+GA]=1:500$) was added to start the polymerization. The reaction was carried out at 150° C. for 8 h. The product was then dissolved in cold water (4° C.). The resulting solution was heated to 80° C. to precipitate the triblock copolymer and remove other impurities. The precipitation process was repeated three times to purify the polymers. The final product was dried by lyophilization. The triblock gel was prepared by dissolving PLGA-PEG-PLGA in water (23% by weight) and kept at 4° C.

Example 3

In Vitro Rapamycin Release Study

The in vitro rapamycin release profiles from were determined in PBS (pH 7.4) containing 0.2% Tween 80 as described ("Delivery of rapamycin to dendritic cells using degradable microparticles" *J Control Release* 133: 191-197). Three mg of rapamycin-loaded unimolecular micelles ("NPs") or 300 μg of rapamycin in 15 μl DMSO/$H_2O$ (v/v=9/1) were dispersed in 300 μl of triblock gel solution contained in a microfuge tube on ice. The tube was then transferred to a 37° C. incubator. After the gel solidified at 37° C., 1 ml of PBS was added. At the indicated time points, microfuge tubes were spun at 22,800×g for 5 min to separate the supernatant from the NPs/gel mixture; the supernatant was collected and replaced with fresh PBS buffer. The supernatant was filtered (membrane pore size 200 nm) to remove any uncollected NPs. The rapamycin concentration in the supernatant was then analyzed by HPLC. Results are shown in FIG. 1. The release of rapamycin from Pluronic gel (PLoS One. 2014 February 21;9(2):e89227) is included for comparison. In vivo, the application of rapamycin in Pluronic gel initially inhibited IH, but the disease reoccurred by four weeks. Id.

As shown in FIG. 1, the bulk of the rapamycin was released from Pluronic gel within 3 days. About half of the rapamycin in the NPs alone was released in the first few days, with remainder being slowly released until the 60 day mark. Rapamycin alone in the triblock gel was released slowly over the first 30 days, and then quickly as the triblock presumably disintegrated over the following few days. In contrast, the present drug delivery system (NPs plus triblock gel) provided sustained release of rapamycin over 120 days.

Example 4

Rat Carotid Artery Balloon Injury and In Vivo Drug Delivery

Male Sprague-Dawley rats (~350 g) underwent carotid artery balloon injury. Briefly, after induction of anesthesia with isoflurane, a longitudinal incision was made in the neck. A 2-F balloon catheter (Edwards Lifesciences, Irvine, Calif.) was inserted through the left external carotid artery and inflated to a pressure of 2 atm to simulate the angioplasty procedure. Blood flow was re-established after injury. Rapamycin or rapamycin-NPs (100 µg rapamycin per 100 g body weight) was dissolved in 300 µl of triblock gel which remained as liquid on ice. The gel solution was then applied around the outside of the injured segment of carotid artery. The gel solidified immediately after exposure to body temperature.

Morphometric study was performed using H&E-stained paraffin sections of the carotid arteries. The areas enclosed by the external elastic lamina (EEL), the internal elastic lamina (IEL), and the luminal area were measured using the NIH Image J software as previously described. Intimal area (IEL area minus luminal area) and medial area (EEL area minus IEL area) and their ratio (I/M ratio) were then calculated. Five sections per animal were used and a mean ±SEM was derived from at least three independent experiments. Data were analyzed by one-way analysis of variance (ANOVA). If significant, the ANOVA was followed by Tukey's multiple comparison test. P values less than 0.05 are considered statistically significant.

Figure 2A:
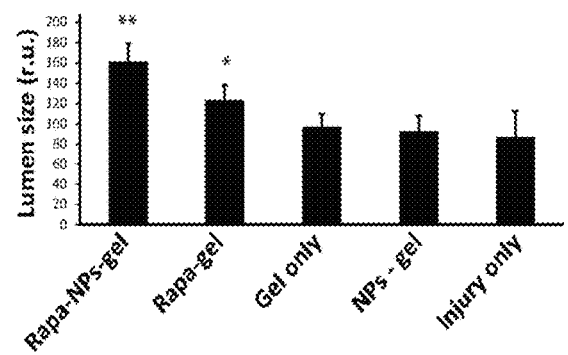
FIGS. 2A-D show quantification of lumen size (2A), intimal area (2B), intimal hyperplasia (intimal to media ratio or I/M) (2C) and media area (2D) in rat carotid arteries three months after injury and drug application as in Example 2. Data are presented as mean±SEM from 5 animals in each group (*P<0.05, **P<0.01 compared to injury only).
Figure 2B:
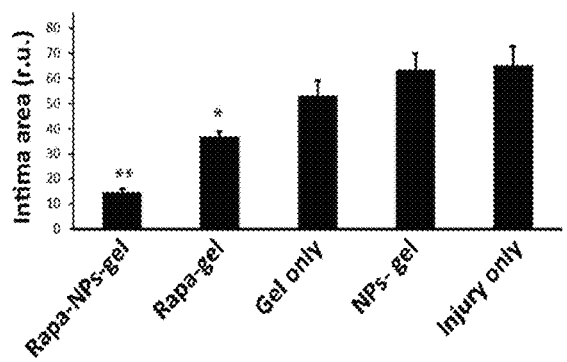
Figure 2C:
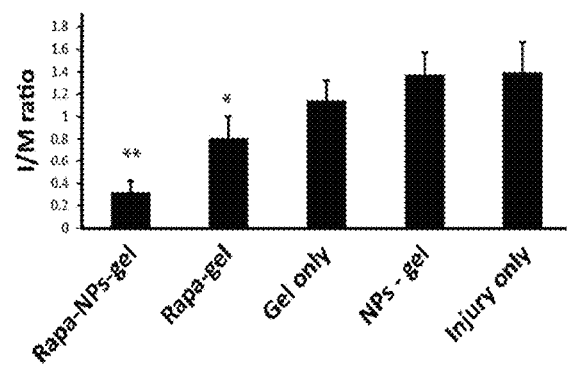
Figure 2D:
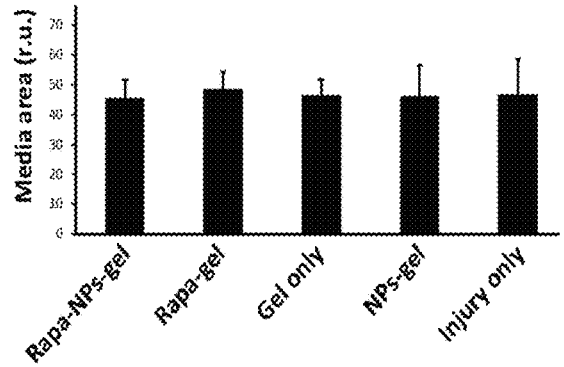
Figure 3:
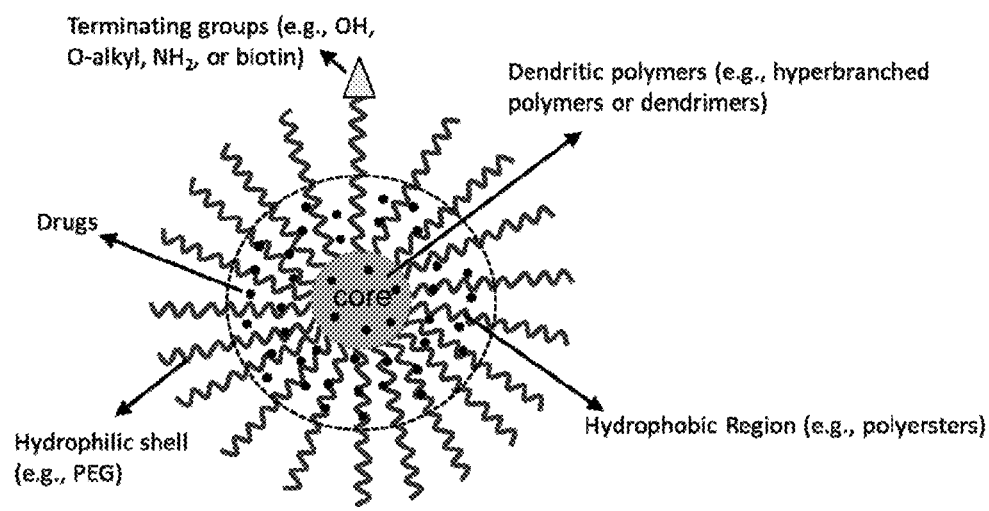
FIG. 3 shows a schematic of an illustrative embodiment of a drug-loaded unimolecular micelle of the present technology including a core dendritic polymer attached to hydrophobic polyesters, which in turn are attached to hydrophilic PEG groups and terminating in various functional groups. Hydrophobic anti-stenotic drugs partition into the core and hydrophobic region of the micelle.

Results of the morphometric study of the injured and treated rat carotid arteries after three months are shown in FIGS. 2A-D. Treatment of the injured arteries with the drug delivery system of the present technology (designated "Rapa-NPS-gel") provided a statistically significant anti-stenotic effect with larger lumen size (FIG. 2A), lower intima area (FIG. 2B) and therefore the lowest I/M ratio (FIG. 2C). FIG. 2D shows that the media area remained roughly similar under all test conditions and therefore unaffected. In summary, three months after application of the present drug delivery system, intimal hyperplasia was still profoundly inhibited (~80%), and the inhibitory effect is significantly greater than rapamycin loaded in the gel without using the present technology.

EQUIVALENTS

While certain embodiments have been illustrated and described, a person with ordinary skill in the art, after reading the foregoing specification, can effect changes, substitutions of equivalents and other types of alterations to the conjugates and micelles of the present technology or derivatives, prodrugs, or pharmaceutical compositions thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, conjugates, reagents, compounds, compositions, labeled compounds or biological systems, which can, of course, vary. All methods described herein can be performed in any suitable order unless otherwise indicated herein or otherwise clearly contradicted by context. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof. No language in the specification should be construed as indicating any non-claimed element as essential.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member, and each separate value is incorporated into the specification as if it were individually recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A composition comprising a hydrogel, unimolecular micelles dispersed within the hydrogel, and an effective amount of anti-stenotic drug dispersed within the unimolecular micelles, wherein
 the hydrogel is a di-or tri-block copolymer comprising one block of poly(ethylene glycol) (PEG) and one or two blocks of poly(lactic-co-glycolic acid) (PLGA), wherein the hydrogel is a PLGA-b-PEG-b-PLGA copolymer having a molecular weight of 2,500 to 3,500 Da, wherein the hydrogel is a thermogel that is water soluble below a gelation temperature of from about 10° C. to about 20° C., and wherein the thermogel forms a stable thermogel above the gelation temperature;
 the unimolecular micelle comprises
  a polyamidoamine (PAMAN) having a molecular weight of 500 to 10,000 Da,
  hydrophobic block polymers attached to at least a majority of the terminating groups of the dendritic polymer, wherein the hydrophobic block polymers have a molecular weight from about 1,000 to about 5,000 Da and which are selected from the group consisting of poly(valerolactone) (PVL), poly(valerolactone-co-lactic acid) (PVCL), and poly(caprolactone) (PCL), and
  poly(ethylene glycol) attached to the hydrophobic block polymer and terminating in OH, O-alkyl, NH2, or biotin, and having a molecular weight of about 1,000 to about 15,000 Da; wherein the unimolecular micelle comprises PAMAM-PVL-PEG-O(C1-3 alkyl) and has a molecular weight of about 100,000 to about 350,000 Da, wherein the PAMAM is a 4-generation dendrimer; and
 the anti-stenotic drug is selected from the group consisting of rapamycin, resveratrol, halofuginone, idarubicin, (S)-tent-butyl 2-(4-(4-chlorophenyl)-2,3,9-trimethyl-6H-thieno[3,2-f][1,2,4]triazolo[4,3-a][1,4]diazepin-6-yl)acetate, 1-[5-(4-Amino-7-methyl-7H-pyrrolo[2,3-d]pyrimidin-5yl)indolin-1-yl]-2-(3-trifluoromethylphenyl)ethanone, and a combination of any two or more thereof.

2. The composition of claim 1 wherein the each PLGA block comprises from 1:4 to 4:1 lactic acid to glycolic acid residues on a molar basis.

3. The composition of claim 1 wherein the each PLGA block comprises from 2:1 to 4:1 lactic acid to glycolic acid residues on a molar basis.

4. The composition of claim 1 wherein the anti-stenotic drug is rapamycin.

5. The composition of claim 1 wherein the loading of anti-stenotic drug is about 1 to about 35 wt % of the unimolecular micelles.

6. The composition of claim 1 wherein the loading of anti-stenotic drug is about 15 to about 25 wt % of the unimolecular micelles.

7. The composition of claim 1, wherein the composition is for delivery to a blood vessel.

* * * * *